(12) United States Patent
Shimasaki et al.

(10) Patent No.: US 7,184,894 B2
(45) Date of Patent: Feb. 27, 2007

(54) QUANTITATIVE MEASUREMENT METHOD AND QUANTITATIVE MEASUREMENT CHIP FOR TARGET SUBSTANCE

(75) Inventors: Takaaki Shimasaki, Kyoto (JP); Akinori Yokogawa, Kyoto (JP)

(73) Assignee: Rohm Co., Ltd, Kyoto (JP)

( * ) Notice: Subject to any disclaimer, the term of this patent is extended or adjusted under 35 U.S.C. 154(b) by 0 days.

(21) Appl. No.: 10/560,311

(22) PCT Filed: Apr. 9, 2004

(86) PCT No.: PCT/JP2004/005191

§ 371 (c)(1),
(2), (4) Date: Dec. 9, 2005

(87) PCT Pub. No.: WO2004/111640

PCT Pub. Date: Dec. 23, 2004

(65) Prior Publication Data

US 2006/0276975 A1    Dec. 7, 2006

(30) Foreign Application Priority Data

Jun. 12, 2003  (JP) .............................. 2003-167792

(51) Int. Cl.
*G01N 21/25*  (2006.01)
(52) U.S. Cl. ............................. 702/23; 422/56; 422/58; 424/499; 137/833; 210/198.2
(58) Field of Classification Search .................. 702/23; 422/51, 56, 57, 58, 60, 61, 70; 424/499; 210/198.2; 137/833
See application file for complete search history.

(56) References Cited

U.S. PATENT DOCUMENTS

| | | | | |
|---|---|---|---|---|
| 4,061,466 A | * | 12/1977 | Sjoholm et al. | 436/535 |
| 4,379,775 A | * | 4/1983 | Brandstetr et al. | 422/51 |
| 4,486,537 A | * | 12/1984 | Koyama et al. | 436/170 |
| 4,820,490 A | * | 4/1989 | Morris | 422/58 |
| 5,840,340 A | * | 11/1998 | Milstein et al. | 424/499 |
| 6,352,578 B1 | * | 3/2002 | Sakata et al. | 96/134 |

(Continued)

FOREIGN PATENT DOCUMENTS

JP    H08-122320 A    5/1996

(Continued)

*Primary Examiner*—Carol S. W. Tsai
(74) *Attorney, Agent, or Firm*—Shinjyu Global IP

(57) ABSTRACT

The present invention provides a quantitative measurement method and quantitative measurement chip which can perform quantitative measurement of a target substance in a short period of time. The invention provides a quantitative measurement method in which a three dimensional mesh structure material is formed, and quantitative measurements are taken of the target substance using a structure which contains a reagent that reacts with the target substance in the mesh. This method includes a contacting step in which a test specimen which includes the target substance is brought into contact with the structure; a detecting step which, in a process in which a substance whose quantity will increase or decrease by means of the reaction between the target substance and the reagent, detects the substance whose quantity is increasing or decreasing within the structure at a contact interface between the test specimen and the reagent; and a quantitative measurement step which performs quantitative measurement of the target substance based on the results of the detecting step. The mesh structure will allow at least the target substance to pass therethrough.

13 Claims, 9 Drawing Sheets

U.S. PATENT DOCUMENTS

| | | |
|---|---|---|
| 6,413,550 B1 * | 7/2002 | Milstein et al. ............. 424/499 |
| 6,657,614 B1 * | 12/2003 | Ito et al. ..................... 345/168 |
| 7,033,603 B2 * | 4/2006 | Nelson et al. ............. 424/426 |
| 2004/0028655 A1 * | 2/2004 | Nelson et al. ............. 424/93.2 |
| 2004/0121420 A1 * | 6/2004 | Smith .......................... 435/18 |
| 2005/0213868 A1 * | 9/2005 | Cunningham ................ 385/12 |
| 2006/0091051 A1 * | 5/2006 | Takada et al. ........... 210/198.2 |
| 2006/0193769 A1 * | 8/2006 | Nelson et al. ............. 424/1.11 |

FOREIGN PATENT DOCUMENTS

JP  2003-057225 A  2/2003

\* cited by examiner $t = t_0 + \Delta t_1$

QUANTITATIVE MEASUREMENT METHOD AND QUANTITATIVE MEASUREMENT CHIP FOR TARGET SUBSTANCE

TECHNICAL FIELD

The present invention relates to a quantitative measurement method and a quantitative measurement chip for a target substance.

PRIOR ART

Biochemical analysis in which enzymes active in the liver, kidneys, and pancreas, as well as reaction products thereof, are sampled from whole blood, and their concentrations measured, have become widely used in order to diagnose liver and bile duct diseases as well as alcohol induced liver damage. For instance, a target substance will be detected and evaluated by biochemical analysis such as the ion selective electrode method, the enzyme method, or the colorimetry method. Biochemical analysis based on colorimetry is a method where the concentration of a specific substance is calculated using the absorption properties of light wavelengths specific to that substance. In other words, the concentration of a specific substance is calculated from the measurement of the quantity of light absorbed by using a calibration curve which determines the correlation between the quantity of light absorbed and the concentration of that specific substance.

A method for detecting the enzyme γ-GTP in order to diagnose alcohol induced liver damage using conventional measurement equipment will be described below. A whole blood specimen is taken from the body and placed in a centrifuge separator at 3000 rpm for 10 to 15 minutes. The centrifugally separated whole blood is divided into a blood cell component and a blood plasma component, and a measurement is performed using the blood plasma component. Furthermore, blood serum in which blood clotting factors such as fibrinogen and prothrombin have been removed from the blood plasma component may be used. In further detail, the measurement is performed as shown below.

7 μL of centrifugally separated blood plasma and 200 μL of 64.3 mM glycylglycine buffer solution were accurately measured using a pipette, and placed in a reaction cell made from a transparent substance with an optical path length of between 5 and 10 mm. The blood plasma and the buffer solution in the reaction cell were mixed to uniformity at 37° C. Five minutes later, 50 μL of a 15.4 mM L-γ-glutamyl-3-carboxy-4-nitroanylide was accurately measured in a pipette and added as a base liquid to the reaction cell and mixed to uniformity. Next, the reaction was performed for 1.4 minutes. At this time, 5-amino-2-nitrobenzoate was produced as shown in reaction formula (1).

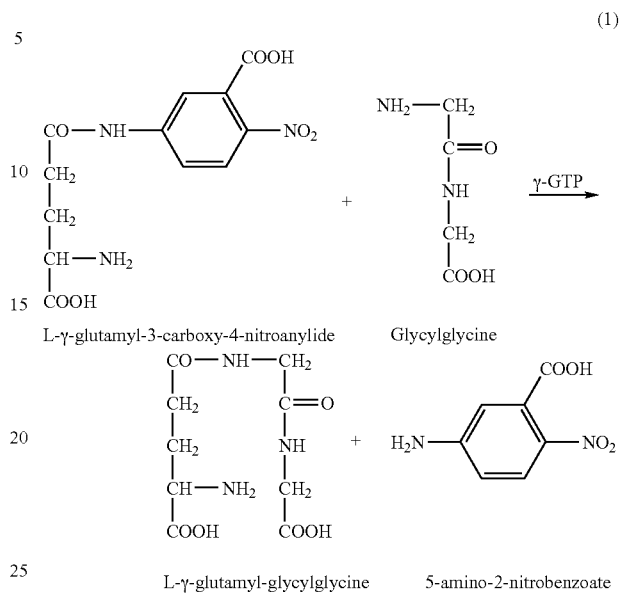

(Reaction Formula 1)

Next, the reaction cell was irradiated with 405 nm wavelength light for 3.6 minutes using a calorimeter such as a multi-wavelength calorimeter, and the amount of light absorbed was measured at 2 to 20 second intervals. The benzene ring which forms the 5-amino-2-nitrobenzoate reaction product specifically absorbs light at a wavelength of 405 nm. Thus, the concentration of 5-amino-2-nitrobenzoate is detected by measuring light absorbance. Furthermore, a correlation exists between the concentration of 5-amino-2-nitrobenzoate and the concentration of the enzyme γ-GTP produced thereby, so the concentration of γ-GTP can be detected from the concentration of 5-amino-2-nitrobenzoate using a calibration curve which determines this correlation. In this manner, γ-GTP activity per liter of whole blood can eventually be calculated.

A conventional ultra-compact biochemical measurement chip for γ-GTP is disclosed in 2002 International Conference on Solid State Devices and Materials, 328–329, 2002. FIG. 13 shows the aforementioned biochemical measurement chip presented in 2002 International Conference on Solid State Devices and Materials, 328–329, 2002. The biochemical measurement chip is a 2 cm square transparent PET (polyethylene terephthalate) substrate 1, and a 40 μm wide, 100 μm deep, 1.6 mm long measurement flow path 2 and a reference flow path 3 are formed in the PET substrate 1.

The method for detecting the γ-GTP enzyme using the aforementioned biochemical measurement chip will be described below. First, 1 mL of a base agent containing buffer solution, 12 mM L-γ-glutamyl-p-N-ethyl-N-hydroxyethyl aminoanylide and 0.2 mM of potassium 1-naphthol-2-sulfonate was placed in the measurement flow path 2 and the reference flow path 3, and heated for 3 minutes at 37° C. The buffer solution was a 50 mM boric acid buffer solution with a glycylglycine concentration of 50 mM. Furthermore, 0.5 μL of centrifugally separated blood serum was added to only the measurement flow path 2 and allowed to react for 15 minutes at 37° C. Furthermore, 1.2 mL of 8.8 mM periodic acid was added. By this operation, a blue color was produced as shown by Reaction Formulas (2) and (3).

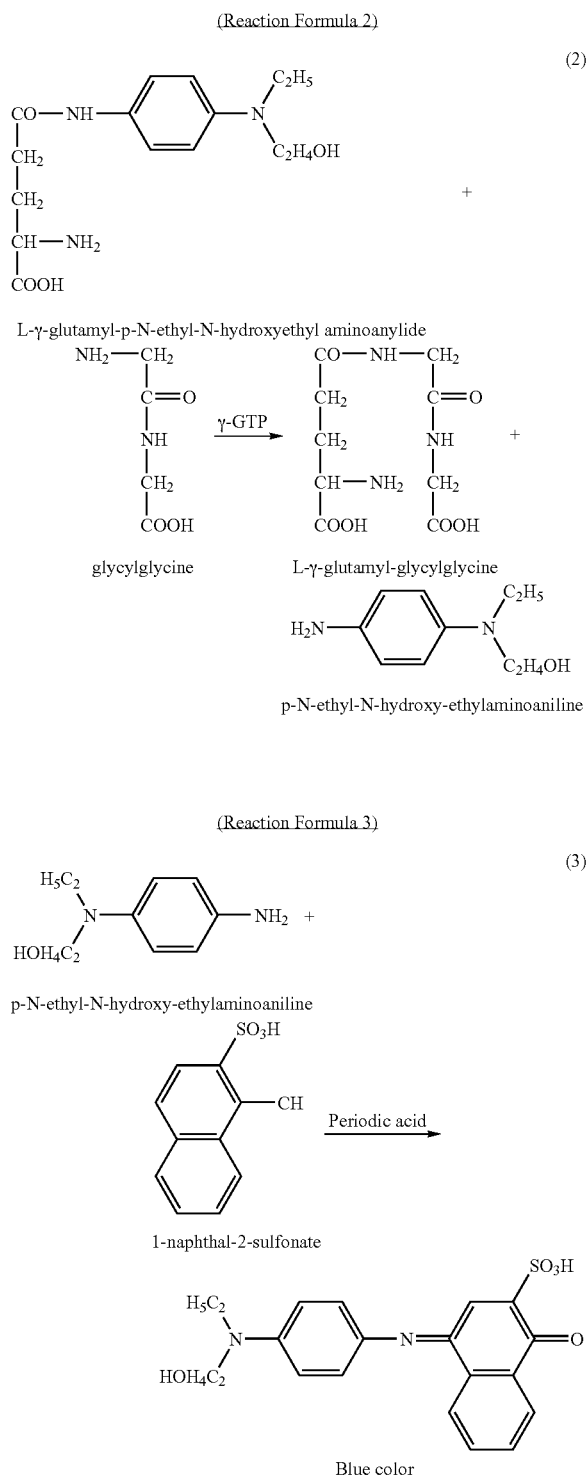

Light with a wavelength of 660 nm was irradiated in the measurement flow path 2 and the reference flow path 3 through a 100 μm diameter pinhole, and the amount of light absorbed in both flow paths was compared. The blue color will only be generated in the measurement flow path 2, so the quantity of light absorbed in the measurement flow path 2 will be greater. The concentration of γ-GTP is calculated from the increase in the quantity of light absorbed.

However, measurement devices for performing biochemical measurements in hospitals and blood measurement centers are large and extremely expensive. Furthermore, the measurement method is complicated, and therefore the measurement is performed by a special clinical measurement technician, and the measurement results will be returned in one week or more.

In addition, the measurement flow path 2 and the reference flow path 3 of the biochemical measurement chip presented in 2002 International Conference on Solid State Devices and Materials, 328–329, 2002 are precision microflow paths, and therefore the ratio of the surface area to the volume of the fluid introduced is large. Thus, the surface tension of the fluid will have a strong effect, mixing the blood serum and the reagent to uniformity in the microflow path will be difficult, and the reaction between the blood serum and the test reagent will be difficult to promote.

Furthermore, in order to accurately determine the concentration of 5-amino-2-nitrobenzoate, the solution in the flow path of the reaction cell or the biochemical measurement chip must be uniform. Moreover, with the conventional test specimen quantitative measurement method, the volume of blood plasma, buffer solution, and base liquid collected must be precisely the same as when the calibration curve was determined. In other words, the quantity of reaction products will vary depending on the quantity of base and blood plasma, so the quantity of the blood plasma or blood serum (the test specimen) and the quantity of the base L-γ-glutamyl-3-carboxy-4-nitroanylide must be accurately collected at the same ratio as when the calibration curve was determined. However, accurately collecting minute quantities of blood plasma or blood serum is difficult.

In addition, when detecting a substance with the colorimetry method using light, the quantity of light transmission can not accurately be measured if blood cell components, namely white blood cells and red blood cells or the like, are present because of the light scattering effect of the blood cells. Therefore, the whole blood collected must be separated into a blood cell component and a blood plasma component by centrifugal separation, and only the blood plasma component removed and reacted with the reagent. Furthermore, there is also a problem with leaking during transport and use of the reagent which is inserted into the reaction cell or the flow path. Moreover, development of ultra-compact biochemical measurement chips has become active in recent years.

Thus, an object of the present invention is to provide a quantitative measurement method and quantitative measurement chip which can perform quantitative measurement of a target substance in a short period of time.

Another object of the present invention is to provide a quantitative measurement method and quantitative measurement chip which can simplify quantitative measurement of a target substance.

Yet another object of the present invention is to provide a quantitative measurement method and quantitative measurement chip which can accurately perform quantitative measurement of a target substance.

Yet another object of the present invention is to provide a quantitative measurement method and quantitative measurement chip which can prevent leaking of the reagent.

DISCLOSURE OF THE INVENTION

In order to resolve the aforementioned problems, a first a first aspect of the present invention is a quantitative measurement method which uses a structure formed with a material having a three dimensional mesh structure, and which contains a reagent which reacts with a target substance in the mesh, to perform quantitative measurements of the target substance. The method comprises a contacting step in which a test specimen containing the target substance is brought into contact with the structure; a detecting step which detects, at a contact interface between the test specimen and the reagent, a substance whose quantity increases or decreases within the structure by means of the reaction between the target substance and the reagent; and a quantitative measurement step which performs quantitative measurement of the target substance in response to the results of the detecting step; wherein the mesh structure allows at least the target substance to pass therethrough.

The target substance is diffused into the structure and reacted with a reagent contained in the mesh structure by causing a test specimen which contains the target substance to come into contact with the three dimensional mesh structure. In other words, the structure which contains the reagent is the reaction site for the target substance and the reagent, a substance whose quantity increases or decreases by means of the reaction between the target substance and the reagent will be detected during this reaction process, and the target substance will be quantitatively measured based on these detection results. At this time, the quantitatively increasing or decreasing substance will be detected, for instance, by means of the distance that the quantitatively increasing or decreasing substance has diffused from the contact interface between the test specimen and the structure. In this manner, the substance whose quantity increases or decreases as the target substance reacts with the reagent will be quantitatively measured while diffusing into the structure, so the quantitative measurement of the target substance can be performed in a short period of time without waiting for equilibrium of the reaction. Furthermore, the quantitative measurement of the target substance is performed based on the diffusion of the target substance in the structure, and the reaction between the diffused target substance and the reagent. More specifically, a quantitative measurement of the target substance is performed based on a correlative relationship between the distance the target substance has diffused into the structure and the concentration of the target substance. Therefore, accurately measuring the quantity of a test specimen that includes a target substance is not necessary, and therefore quantitative measuring of the target substance can be simplified.

Furthermore, removing substances other than the target substance from the test specimen by centrifugal separation or the like is not necessary because the target substance will specifically react with the reagent. Thus, quantitative measurement of the target substance is convenient and can be performed in a short period of time.

A second aspect of the present invention provides a quantitative measurement method according to the first aspect of the present invention, in which the mesh structure has a size which prevents a specimen which is larger than the target substance from passing therethrough.

The mesh structure has a size which allows the target substance to pass therethrough, but prevents a test specimen which is larger than the target substance to flow therethrough, so the target substance which is subject to quantitative measurement will diffuse into the mesh and essentially react uniformly with the reagent. Therefore, uniformly mixing the reagent with the test specimen which contains the target substance is not necessary. Furthermore, interference by a test specimen which is larger than the target substance can be prevented when detecting the substance whose quantity increases or decreases by means of the reaction. For instance, light scattering caused by a test specimen which is larger than the target substance can be prevented from hindering accurate measurement of the light transmissivity. Furthermore, the reagent is contained in the mesh structure, so leaking of the reagent can be prevented.

Furthermore, a test specimen larger than the target substance will not diffuse into the mesh structure and will not hinder the quantitative measurement of the target substance, and the target substance will specifically react with the reagent, so removing substances other than the target substance or a test specimen which is larger than the target substance from the test specimen by centrifugal separation or the like is not necessary. Thus, quantitative measurement of the target substance is convenient and can be performed in a short period of time.

A third aspect of the present invention provides a quantitative measurement method according to the first aspect of the present invention, in which the test specimen is whole blood and the target substance is the blood plasma component thereof.

When whole blood (the test specimen) comes into contact with the structure, the blood plasma component will pass through the mesh structure and will react with the reagent in the structure. At this time, components of the test specimen which are larger than the blood plasma component, such as the blood cell component, will not be able to pass through the mesh structure. Thus, the effects of the blood cell component on absorbance and scattering or the like will be reduced when using the colorimetry method to detect the substance whose quantity increases or decreases by means of the reaction between the target substance and the reagent. Thus, quantitative measurement of the target substance can be accurately performed without requiring separation of the blood cells.

A fourth aspect of the present invention provides a quantitative measurement method according to the first aspect of the present invention, in which in the detection step, the concentration of the quantitatively increasing or decreasing substance is measured at a predetermined distance from the contact interface between the test specimen and the structure, after a predetermined period of time has elapsed from the time at which the test specimen came into contact with the structure in the contacting step.

The diffusion speed of the target substance into the structure will increase as the concentration of the target substance increases, so a substance whose quantity increases by means of the reaction between the target substance and the reagent will be detected at high concentrations, and a substance whose quantity decreases by means of the reaction between the target substance and the reagent will be detected at low concentrations. Thus, quantitative measurements of the target substance can be performed from the concentration of a substance whose quantity increases or decreases by means of the reaction between the target substance and the reagent, at a predetermined distance from the contact interface after a predetermined period of time has elapsed.

A fifth aspect of the present invention provides a quantitative measurement method according to the first aspect of the present invention, in which in the detection step, the time until the predetermined concentration of a quantitatively increasing or decreasing substance is detected at a predetermined distance from the contact interface between the test specimen and the structure will be measured, based upon the time at which the test specimen first came into contact with the structure in the contacting step.

The diffusion speed of the target substance into the structure will increase as the concentration of the test substance increases, so the substance whose quantity increases or decreases by means of the reaction between the target substance and the reagent will be detected in a short period of time at a certain distance away from the contact interface. Thus, quantitative measurement of the target substance can be performed from the time at which the quantitatively increasing or decreasing substance is detected at a predetermined concentration at a predetermined distance from the contact interface.

A sixth aspect of the present invention provides a quantitative measurement method according to the first aspect of the present invention, in which in the detection step, the distance from the contact interface between the test specimen and the structure to the position where the quantitatively increasing or decreasing substance is detected will be measured, after a predetermined period of time has elapsed from the time at which the test specimen first came into contact with the structure in the contacting step.

The diffusion speed of the target substance into the structure will increase as the concentration of the target substance increases, so the range in which a substance will be detected whose quantity increases or decreases by means of the reaction between the target substance and the reagent will become larger. Thus, a target substance can be quantitatively measured by measuring the location at which the quantitatively increasing or decreasing substance is detected after a predetermined period of time has elapsed.

A seventh aspect of the present invention provides a quantitative measurement method according to the first aspect of the present invention, in which in the detection step, the concentration distribution of the quantitatively increasing or decreasing substance is detected at a distance from the contact interface between the test specimen and the structure by scanning the structure after the contacting step.

The diffusion speed of the target substance into the structure will increase as the concentration of the target substance increases, so the concentration gradient of the concentration distribution will be steep. Thus, quantitative measurement of the target substance can be made by detecting the concentration distribution of the quantitatively increasing or decreasing substance.

An eighth aspect of the present invention provides a quantitative measurement method according to the first aspect of the present invention, in which in the detection step, the quantitatively increasing or decreasing substance is detected by measuring the light absorbency of the quantitatively increasing or decreasing substance.

A ninth aspect of the present invention provides a quantitative measurement method according to the first aspect of the present invention, further comprising a diffusion promoting step which promotes the diffusion of a target substance into the structure by applying a voltage to a target substance having an electrical charge.

High-speed diffusion of a target substance into the structure is possible by applying a voltage to a target substance having an electrical charge. Thus, quantitative measurement of the target substance can be performed in an even shorter period of time.

A tenth aspect of the present invention provides a quantitative measurement chip comprising a reaction cell having a structure which is formed with a three dimensional mesh structure material, the structure containing a reagent that reacts with a target substance in the mesh; a photoreceptor and photoemitter for measuring, at a contact interface between the test specimen and the reagent, the light absorbance of a substance whose quantity increases or decreases within the reaction cell by means of the reaction between the target substance and the reagent; and an injection tube for injecting a test specimen containing the target substance into the reaction cell. The mesh structure allows at least the target substance to pass therethrough.

In the aforementioned quantitative measurement chip, the target substance is diffused in the structure and reacts with a reagent contained in the mesh structure. In other words, the structure which contains the reagent is the reaction site for the target substance and the reagent, the substance whose quantity increases or decreases due to the reaction between the target substance and the reagent is detected during this reaction process, and the target substance is quantitatively measured based on these detection results. At this time, the quantitatively increasing or decreasing substance is detected, for instance, by the distance the quantitatively increasing or decreasing substance has diffused from the contact interface between the test specimen and the structure. In this manner, the quantitatively increasing or decreasing substance is quantitatively measured in a process where the target substance reacts with the reagent while diffusing into the structure, so the quantitative measurement of the target substance can be performed in a short period of time without waiting for the reaction to reach equilibrium. Furthermore, quantitative measurement of the target substance is performed based on the diffusion speed, so accurately measuring the quantity of reagents including the target substance is not necessary, and quantitative measuring of the target substance can be simplified.

The target substance, together with the test specimen which contains the target substance, is injected into the reaction cell through the injection tube. Therefore, even though the quantity of target substance is minute, the flow path resistance in the injection tube will be minimal for the entire test specimen, so the target substance can easily be injected into the reaction cell.

In addition, the reagent is contained in the mesh structure, which is formed from a three dimensional mesh structure material, so leaking of the reagent during transport or use can be prevented.

Furthermore, removing substances other than the target substance from the test specimen by centrifugal separation or the like is not necessary because the target substance will specifically react with the reagent, and therefore quantitative measurement of the target substance is convenient and can be performed in a short period of time.

An eleventh aspect of the present invention provides a quantitative measurement chip according to the tenth aspect of the present invention, in which the mesh structure has a size which prevents a test specimen that is larger than the target substance from passing therethrough.

The mesh structure has a size which allows the target substance to pass therethrough but prevents a test specimen which is larger than the target substance to pass therethrough, so the target substance which is subject to quantitative measurement will diffuse into the mesh and essentially react uniformly with the reagent. Therefore, uniformly mixing a reagent with the test specimen that contains the target substance is not necessary. In addition, interference by a test specimen which is larger than the target substance in the detection of the substance whose quantity increases or decreases by means of the reaction can be prevented. Fur thermore, by not allowing a test specimen larger than the target substance to diffuse into the mesh structure and not hindering the quantitative measurement of the target substance, and specifically reacting the target substance with the reagent, removing components which are larger than the target substance from the test specimen by centrifugal separation or the like is not necessary, quantitative measurement of the target substance will be convenient, and can be performed in a short period of time.

A twelfth aspect of the present invention provides a quantitative measurement chip according to the tenth aspect of the present invention, in which the planar direction of the photoemission surface of a photoemitter and the planar direction of the photoreception surface of a photoreceptor intersect with the planar direction of the contact interface.

A thirteenth aspect of the present invention provides a quantitative measurement chip according to the tenth aspect of the present invention, in which the photoemitter and the photoreceptor are respectively formed from a photoemission hole for irradiating light on the structure and a photoreception hole which receives light from the structure.

To illustrate, in situations in which the film thickness of the quantitative measurement chip is thin and the length of the light path cannot be maintained at a sufficient length in order to measure light absorbance, a sufficient light path length can be maintained and the light absorbency can be measured with good accuracy by measuring the light absorbency inside the reaction cell by means of the photoemission hole and the photoreception hole provided in the quantitative measurement chip.

PREFFERED EMBODIMENTS OF THE INVENTION

Figure 1:
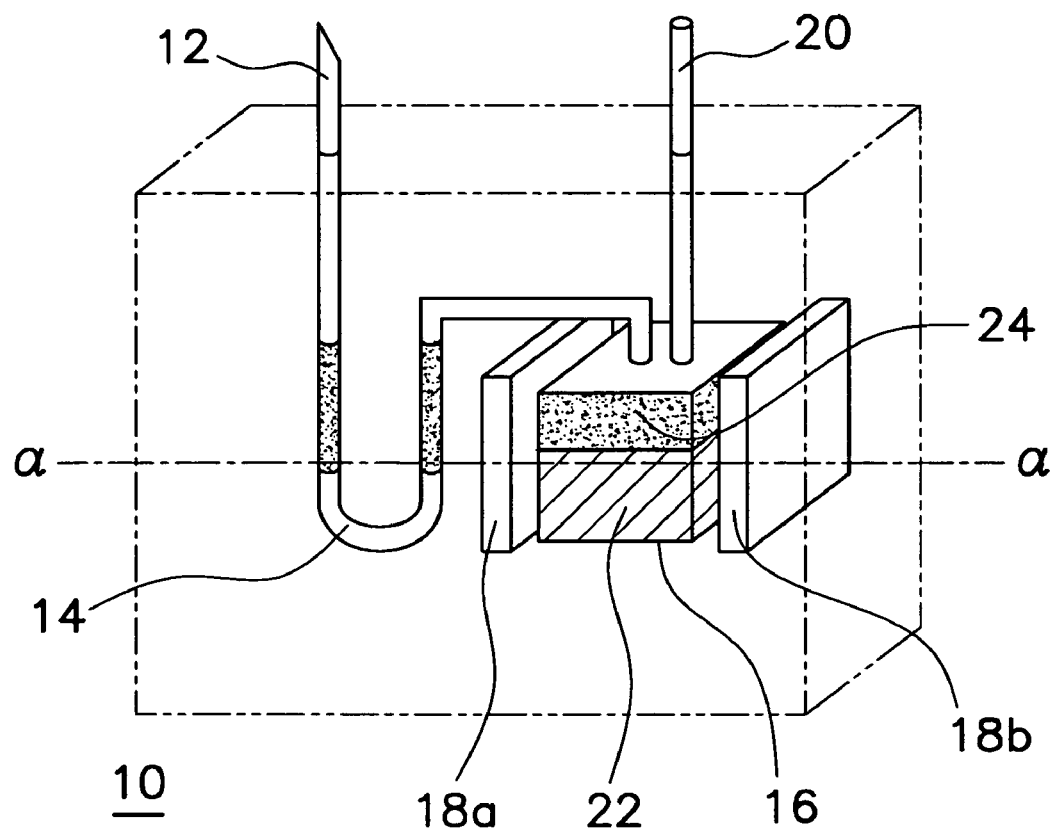
FIG. 1 is a structural diagram of a quantitative measurement chip according to an embodiment of the present invention.
Figure 2:
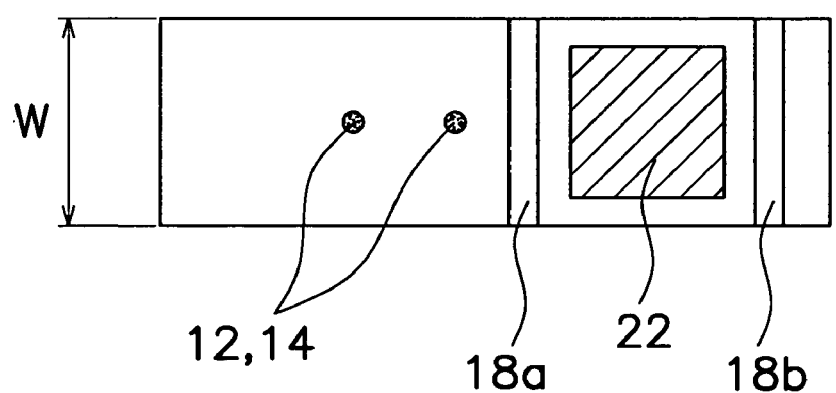
FIG. 2 is a plan view of the cross-section taken along line α—α in FIG. 1.
Figure 3A:
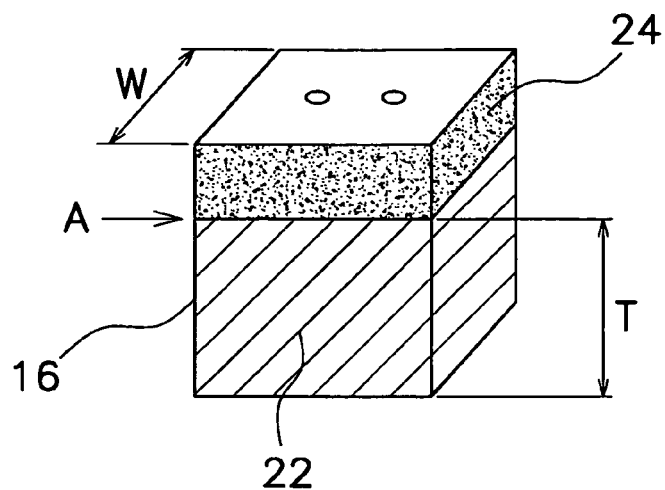
FIG. 3(a) is an expanded diagram of a reaction cell.
Figure 3B:
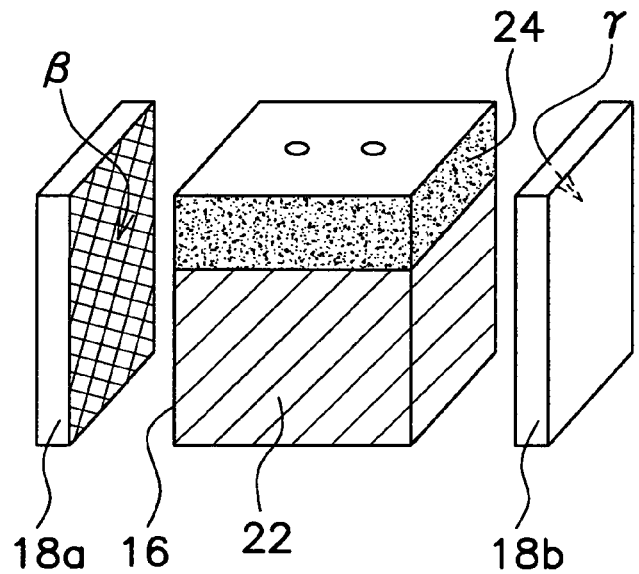
FIG. 3(b) is an expanded diagram of the reaction cell, photoemission hole, and photoreception hole.
Figure 3C:
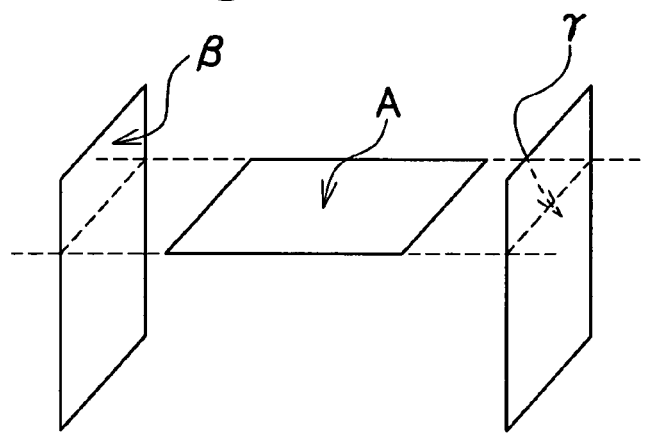
FIG. 3(c) is a descriptive diagram showing the relationship between the photoemission hole and the photoreception hole to a contact interface.

FIG. 1 is a structural diagram of the quantitative measurement chip according to an embodiment of the present invention, FIG. 2 is a plan view of the cross-section taken along line α—α in FIG. 1, FIG. 3(a) is an expanded diagram of a reaction cell, FIG. 3(b) is an expanded diagram of the reaction cell, photoemission hole, and photoreception hole, and FIG. 3(c) is a descriptive diagram showing the relationship between the planar direction of the photoemission hole and the planar direction of the photoreception hole to the planar direction of the contact interface. The structure of the quantitative measurement chip of the embodiment will be described below.

Structure

A quantitative measurement chip 10 is a transparent plastic PET substrate, and has an injection port 12 such as a blood sampling needle, an injection tube 14, a reaction cell 16, an photoemission hole 18a, an photoreception hole 18b, and a discharge port 20. The reaction cell 16 comprises a structure 22 made from a three dimensional mesh structure material, and a contact unit 24 for causing a target substance subject to quantitative measurement to contact with the structure 22. The interface where the target substance is introduced to the contact unit 24 and the target substance and the structure 22 are brought into contact with each other, i.e., the contact interface A in FIG. 3(a), is the reference location for the quantitative measurement of the target substance. Here, the planar direction of the photoemission surface of the photoemission hole 18a which emits light (surface β in FIG. 3(b)), and the planar direction of the photoreceptor surface (surface γ in FIG. 3(b)) which receives light, intersect with the planar direction of the contact interface A. FIG. 3(c) will be used for a more detailed description. FIG. 3(c) is a relational diagram for the contact interface A in the reaction cell, the photoemission surface β of the photoemission hole 18a, and the photoreceptor surface γ of the photoreception hole 18b. As shown in FIG. 3(c), the photoemission hole 18a and the photoreception hole 18b are established such that the planar direction of the photoemission surface β and the planar direction of the photoreceptor surface γ will intersect.

As described above, the photoemission hole 18a and the photoreception hole 18b should be established to intersect the planar direction of the contact interface A so that the light absorbency or the like in the structure 22 can be measured, but the position, shape, and size thereof are not restricted. To illustrate, the photoemission hole 18a and the photoreception hole 18b may be established in part with respect to the structure 22 in order to intersect with the planar direction of the contact interface A. Furthermore, in place of the photoemission hole 18a and the photoreception hole 18b, a main surface and a back surface opposite to the main surface of a quantitative measurement chip 10 which is formed from a transparent material may be used as a light transmitting unit for photoemission and photoreception. At this time, similar to the photoemission hole 18a and the photoreception hole 18b, the light transmitting unit should be established to intersect the planar direction of the contact interface A so that the light absorbency or the like in the structure 22 can be measured, but the position, shape, and size thereof are not restricted. Thus, the entire quantitative measurement chip does not need to be formed from a transparent material, but for instance, may be partially formed from a transparent material so that measurement of the light absorbency in the structure 22 will be possible, and the region formed from transparent material may be used as the light transmitting unit.

As described above, whether the photoemission hole 18a and the photoreception hole 18b are established in the quantitative measurement chip 10 or whether the main surface and the back surface of the quantitative measurement chip 10 are used as a light transmitting unit can be appropriately selected based on the optical path length of the light which passes through into the structure 22. To illustrate, if the film thickness of the structure 22, or in other words the film thickness W in FIG. 3(*a*), is less than between 5 mm and 1 cm, the light absorbency will preferably be measured by the photoemission hole 18a and the photoreception hole 18b. In situations in which the film thickness W is too thin, there is a possibility that the optical path length for the light passing into the structure 22 cannot be sufficiently ensured. Thus, the optical path length can be sufficiently ensured and the absorbency can be accurately measured by measuring the absorbency in the structure 22 through the photoemission hole 18a and the photoreception hole 18b. Furthermore, if the film thickness W is thin, the volume of the structure 22 will be small, so a quantitative measurement can be made even though only a small quantity of the target substance is prepared for injection into the structure 22.

The contact unit 24 in which the target substance is injected should be established such that quantitative measurement of the target substance is possible through the photoemission hole 18a and the photoreception hole 18b, but the position, shape, and size thereof are not restricted.

The length of the structure 22 in the direction which intersects with the contact interface A, or in other words length T in FIG. 3(*a*), can be appropriately set based on the ease of diffusion of the target substance in the gel like substance which forms the structure 22.

The structure 22 is formed with a gel like substance such as agarose or the like as the main material thereof, and contains a reagent which reacts with the target substance. Agarose is a polysaccharide gel like substance with agar—agar as the main ingredient, is highly compatible with biogenic substances, and is highly transparent. Furthermore, the agarose mesh can be adjusted to a size where at least the target substance can pass through. Furthermore, the size of the agarose mesh is preferably adjusted to be impermeable to substances larger than the target substance, and for instance, is set to a size between several tens of nanometers and several hundreds of nanometers. By adjusting the size of the mesh of the gel like substance in this manner, a function can be provided which hinders diffusion into the structure 22 of blood cells (when whole blood is collected as the test specimen), which have diameters larger than that of the blood plasma which is subject to quantitative measurement.

Quantitative Measurement Method

Next, a quantitative measurement method using the aforementioned quantitative measurement chip 10 will be described. A test specimen which contains the target substance is introduced to the injection tube 14 from the injection port 12 of the quantitative measurement chip 10. The test specimen which contains the target substance is injected into the contact unit 24 in the reaction cell 16 by drawing up the test specimen which includes the target substance from the discharge port 20, and causing the test specimen which contains the target substance to contact the structure 22. The mesh structure 22 has a size which allows permeation of at least the target substance, so at least the target substance in the test specimen will be diffused inward from the surface of the structure 22. At this time, components of test specimen, other than the target substance, which are smaller than the web of the structure 22 will diffuse into the structure 22, but will not react with the reagent because of the specificity of the reagent to the reaction. On the other hand, the target substance which is diffused into the structure 22 will specifically react with the reagent which is included in the structure 22.

Quantitative measurement of the target substance is performed by detecting a substance which is consumed by the reaction between the reagent and the target substance, or a substance which is produced by the reaction between the target substance and the reagent, based on the contact interface between the test specimen and the structure 22. In particular, the quantitative measurement of the target substance is performed during the process where the target substance reacts with the reagent while diffusing into the structure 22. Note that the size and shape or the like of the contact interface between the target substance and the structure 22 is not restricted.

Figure 4:
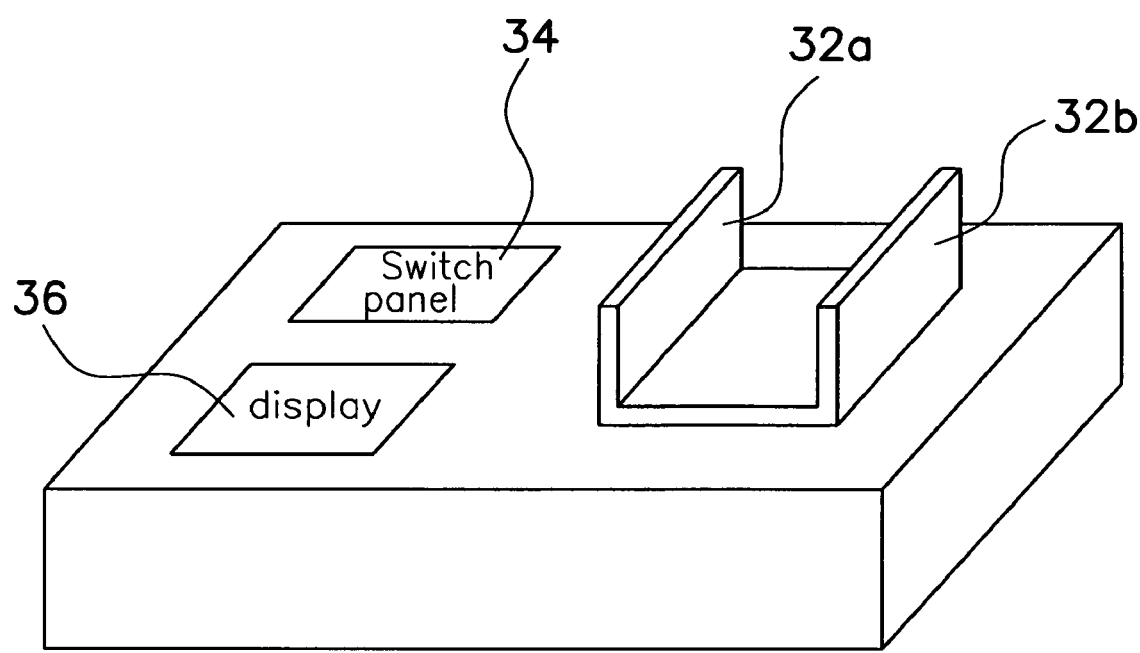
FIG. 4 is an oblique view of a detection device.

Detection of substances which are consumed by the reaction between the target substance and the reagent, or substances which are produced by the reaction between the target substance and the reagent, is performed by irradiating light into the structure 22 through the photoemission hole 18a and receiving the light released from the structure 22 through the photoreception hole 18b. Specifically, a detection device 30 as shown in FIG. 4 may be used. The detection device 30 has for instance a photoemitter 32a, a photoreceptor 32b, a control panel 34, and a display unit 36. The photoemitter 32a and the photoreceptor 32b of the detection device 30 are inserted into the photoemission hole 18a and the photoreception hole 18b which are established in the quantitative measurement chip 10, and then the absorbency in the structure 22 is measured. Measurement of the light absorbency can be performed by methods such as a transmitted beam measurement or a reflected beam measurement.

If the target substance has an electrical charge, a voltage may be applied to the reaction cell 16 where the test specimen containing the target substance is injected in order to diffuse the target substance in the structure 22. Thereby the target substance can be quickly diffused into the structure 22, and quantitative measurement of the target substance can be performed in an even shorter period of time.

As previously described, if the mesh structure 22 is adjusted to a size which will not allow permeation of substances larger than the target substance, substances included in the test specimen which are larger than the size of the mesh of the gel will be restricted by the size of the mesh structure 22 and will not be able to permeate through the mesh. Therefore, at least the target substance subject to quantitative measurement will diffuse through the mesh and essentially uniformly react with the reagent, while the components of test specimen which are larger than the target substance will be prevented from permeating through the mesh. Therefore, uniformly mixing the reagent with the test specimen which contains the target substance is not necessary. To illustrate, even if the target substance is the blood plasma component of whole blood, the blood plasma component will diffuse into the structure 22 without the blood cells in the blood diffusing into the structure 22, so separating the blood plasma component from the whole blood is not necessary. Furthermore, interference by test specimen components which are larger than the target substance can be prevented when detecting a substance whose quantity increases or decreases due to the reaction between the target substance and the reagent. For instance, light scattering caused by blood cells can be prevented from hindering accurate measurement of the light transmissivity.

The quantitative measurement method for the target substance will be described below in detail. With the method shown below, a predetermined calibration curve is calculated based on the increase in the diffusion into the structure of the target substance which is proportional to the concentration of the target substance in the test specimen, and a quantitative measurement of the target substance is performed based on this calibration curve.

Figure 5:
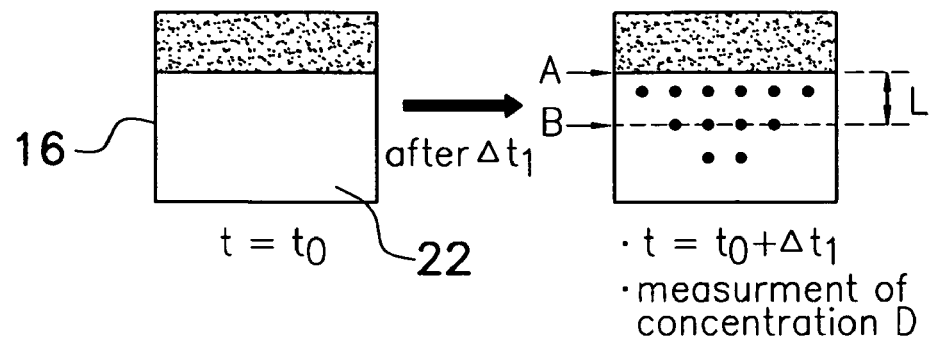
FIG. 5 is a descriptive diagram (1) showing a quantitative measurement method.

With the first method, as shown in FIG. 5, the concentration D of a substance M which is consumed in the reaction between the target substance and the reagent, or the concentration D of a substance M which is produced in the reaction between the target substance and the reagent, is measured from the contact start time (t=t0) when contact between the structure 22 and a test specimen containing the target substance begins, for a predetermined period of time (t=t0+Δt1). The detection point B of the concentration D is located at a point that is a predetermined distance L from the contact interface A of the structure 22 and the test specimen. The diffusion speed of the target substance into the structure 22 will increase at high concentrations of the target substance, so the substances which increase due to the reaction between the target substance and the reagent will be detected at higher concentrations, and the substances which decrease due to the reaction between the target substance and the reagent will be detected at lower concentrations. Detecting the light absorbency rather than detecting the concentration is also acceptable. The concentration of the target substance in the test specimen can be quantitatively measured based on the time from the contact start time, the distance L from the contact interface A, and the concentration of the quantitatively increasing or decreasing substance at detection point B.

Figure 6:
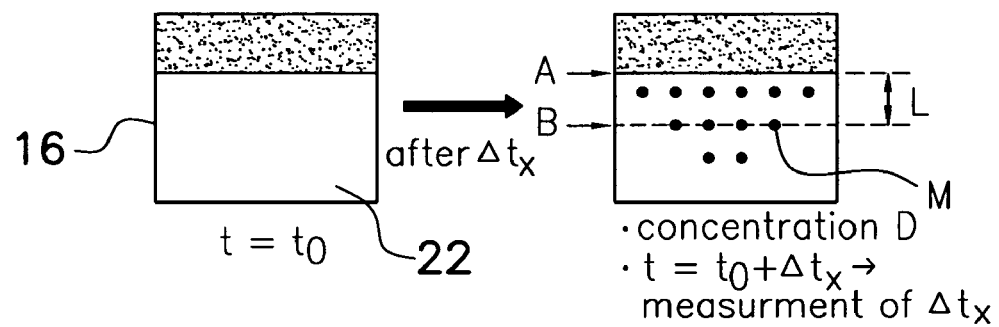
FIG. 6 is a descriptive diagram (2) showing the quantitative measurement method.

With the second method, as shown in FIG. 6, the time (Δtx) is measured until a predetermined concentration D is reached at a detection point B that is a predetermined distance L from the contact interface A between the structure 22 and a test specimen containing the target substance, for a substance M whose quantity is reduced by the reaction between the target substance and the reagent, or for a substance M whose quantity is increased by the reaction between the target substance and the reagent. At this time, the measurement time (Δtx) is measured using the contact start time (t=t0) between the test specimen and the structure as a reference. The diffusion speed of the target substance into the structure 22 will increase at higher concentrations of the target substance, so the time until the predetermined concentration is detected at detection point B for substances whose quantity increases or decreases due to the reaction between the target substance and the reagent will be short. Thus, quantitative measurement of the target substance can be performed for the target substance based on the distance from the contact interface A, and the time from the contact start until a predetermined concentration is detected at a detection point B for the quantitatively increasing or decreasing substance.

Figure 7:
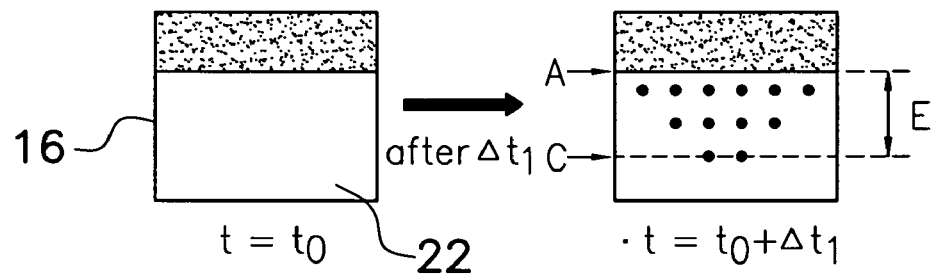
FIG. 7 is a descriptive diagram (3) showing the quantitative measurement method.

With the third method, as shown in FIG. 7, the last point C where the substance M (whose quantity increases or decreases due to the reaction between the target substance and the test specimen) is detected and the detection distance E from the contact interface A is measured after a predetermined period of time has lapsed (t=t0+Δt1) from the contact start time between the test specimen and the structure 22 (t=t0). The diffusion speed of the target substance into the structure 22 will increase at higher concentrations of the target substance, so the detection distance E will be large from the contact interface A of the final point C of the quantitatively increasing or decreasing substance due to the reaction between the target substance and the reagent. Thus, the target substance can be quantitatively measured by measuring the detection distance E from the contact interface A of the point where the quantitatively increasing or decreasing substance is detected, from the contact start time until a predetermined period of time has lapsed.

Figure 8A:
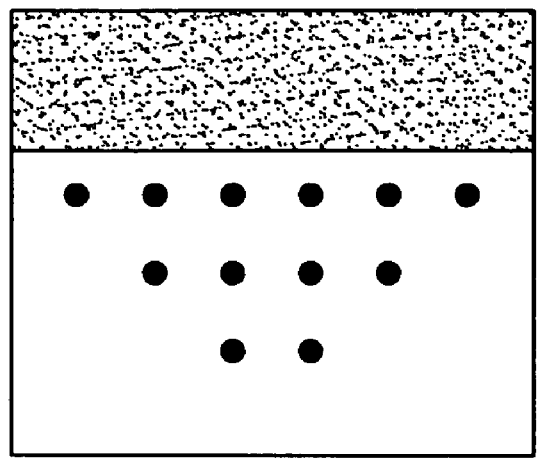
FIG. 8(a) is a descriptive diagram (4) showing the quantitative measurement method.
Figure 8B:
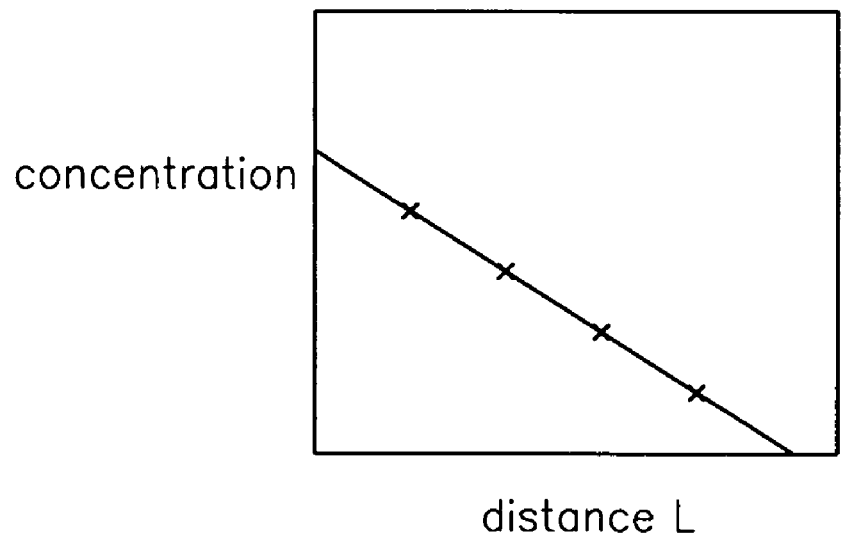
FIG. 8(b) is a descriptive diagram (5) showing the quantitative measurement method.

With the fourth method, as shown in FIG. 8(a), the structure 22 is scanned for a predetermined period of time (t=t0+Δt1) from the contact start time between the test specimen and the structure 22 (t=t0), and a concentration distribution profile for a substance whose quantity increases or decreases due to the reaction between the target substance and the reagent is determined. Furthermore, the concentration distribution of a quantitatively increasing or decreasing substance which corresponds to the scanned profile is detected, and the target substance is quantitatively measured. Furthermore, as shown in FIG. 8(b), the relationship between the distance and the concentration may also be determined from the profile obtained by scanning. Specifically, the concentration distribution is detected for a distance L from the contact interface A between the test specimen and the structure 22 for a substance whose quantity increases or decreases due to the reaction between the target substance and the reagent. The diffusion speed of the target substance into the structure 22 will increase at higher concentrations of the target substance, so the concentration gradient of the concentration distribution will be steep. Thus, quantitative measurement of the target substance can be made by detecting the concentration distribution of the quantitatively increasing or decreasing substance.

As described above, quantitative measurement of the target substance according to this embodiment is performed during the process where the target substance reacts with the reagent while diffusing into the structure 22, but of course the quantitative measurement may be performed even though diffusion of the target substance is finished and after the reaction with the reagent is completed.

Biochemical Measurements

With the present invention, the following biochemical analyses may, for example, be performed.

Measurements which evaluate liver function: lactic dehydrogenase (LDH), AST (GOT), ALT (GPT), alkaline phosphatase (ALP), bilirubin (Bil), total bilirubin (T-Bil), γ-GTP, cholinesterase (ChE), albumin globulin ratio (A/G ratio), LAP, ICG, ZTT, TTT, and the like.

Measurements which evaluate kidney function: urea nitrogen (BUN), creatinine (Cr), uric acid (UA) and the like.

Measurements which evaluate the heart: CPK, LDH, AST (GOT) and the like.

Measurements which evaluate fat: total cholesterol (T-Cho), HDL cholesterol (HDL-Cho), LDL cholesterol (LDL-Cho), triglyceride (TG), free cholesterol (F-Cho) and the like.

Measurements which evaluate the pancreas: amylase (AMY), lipase and the like.

Measurements which evaluate glucose metabolism type I diabetes: glucose, glucohemoglobin (HbAlc), insulin and the like.

Types of Gelatinous Substances

With the present invention, the following gelatinous substances may, for example, be used:

Natural polymer gels (agar—agar, agaropectin, starch, amylase, amylopectin, carageenan, geran gum, xanthan gum, curdlan, gelatin, collagen, alginic acid, pectin, konjak mannan, methyl cellulose, hydroxypropyl cellulose, dextran), synthetic polymer gels (polyethylene, polystyrene, polyacrylate, polyacrylic acid, polymethacrylic acid, polyglutamic acid, polyvinyl pyridine, polyvinyl imidazole, acrylamide, vinyl pyrrolidone, hydroxyethyl methacrylate, o-benzyl-L-glutamate, polyethylene glycol, hyaluronic acid), inorganic materials (porous glass beads, silica gel), latex beads, bead shaped polymer gels (Sephadex, Sephacryl, Sepharose, Bio-Gel) and the like.

In particular, gelatinous substances which do not have ionic functional groups on side chains are preferable when the substance to be quantitatively measured is an enzyme made from proteins, because proteins have electrical charges. Gelatinous substances which are not hydrophobic are even more preferable. Examples may include agarose, dextran, polyvinyl alcohol, cellulose, or acrylamide and the like, derivatives thereof, or bead shaped polymer gels thereof.

Effects

With the quantitative measurement chip 10 of the present invention, the structure 22 which contains the reagent is the reaction site for the target substance and the reagent, the substance whose quantity increases or decreases due to the reaction between the target substance and the reagent is detected during this reaction process, and the target substance is quantitatively measured based on these detection results. In other words, the quantitatively increasing or decreasing substance is quantitatively measured in a process where the target substance is reacting with the reagent while diffusing into the structure 22, so the quantitative measurement of the target substance can be performed in a short period of time without waiting for equilibrium of the reaction. Furthermore, quantitative measurement of the target substance is performed based on the reaction of the target substance which has defused into the structure 22 and the reagent, so accurately collecting the target substance and the test specimen which contains the target substance is not necessary. Thus, quantitative measurement of the target substance can be simplified. In other words, with the present invention, the concentration of the target substance is quantitatively measured using a calibration curve predetermined by the relationship between the concentration of the target substance and the diffusion speed, so accurately collecting the target substance and the test specimen is not necessary. Thus, for instance, even if the quantity of target substance or test specimen containing the target substance is extremely small and accurate collection is difficult, quantitative measurement of the target substance can be accurately performed.

In addition, removing substances other than the target substance from the test specimen by centrifugal separation or the like is not necessary because the target substance will specifically react with the reagent, and therefore quantitative measurement of the target substance is convenient and can be performed in a short period of time. Furthermore, if the mesh structure 22 hinders diffusion into the mesh structure 22 of test specimen components larger than the target substance, test specimen components which are larger than the target substance will not need to be separated and removed by centrifugal separation or the like, so quantitative measurement of the target substance is further simplified and can be performed in a short period of time.

Thus, the target substance together with the test specimen which contains the target substance is injected into the reaction cell 16 through the injection tube 14. Therefore, even though the quantity of target substance is minute, the flow path resistance in the injection tube 14 will be minimal for the entire test specimen, so the target substance can easily be injected into the reaction cell 16.

Furthermore, the reagent is contained in the mesh structure 22 which is formed from the three dimensional mesh structure material, so leaking of the reagent during transport or use can be prevented.

In addition, the light absorbency in the reaction cell 16 is measured and through the photoemission hole 18a and the photoreception hole 18b established in the quantitative measurement chip 10 when the quantitative measurement of the target substance is performed, so the quantitative measurement chip for the target substance can be made lighter and more compact. Furthermore, gel like materials are inexpensive and can be produced from a small quantity of gelatinous reagent. Furthermore, a small quantity of gelatinous reagent is required for a small quantitative measurement chip, so quantitative measurement chips can be provided inexpensively, and therefore the measurement can conveniently be performed at home.

EXAMPLE 1

Using the aforementioned quantitative measurement chip 10 shown above, lactic dehydrogenase (LDH), a marker for improper liver function and myocardium health, was quantitatively measured as the target substance. Agarose was used for the structure 22. Furthermore, the mesh structure 22 which consists of agarose contained pyruvic acid and NADH (reduced nicotinamide adenine dinucleotide), which are reagents for detecting LDH. The method of preparing the structure 22 which contains a reagent including a base material and a buffer solution in the mesh will be described below.

Method of Preparing the Structure

Powdered agarose may have absorbed moisture, and was therefore dried for several minutes in a vacuum dryer. 50 mg of powdered agarose was weighed using a medicine spoon, tweezers, and an electronic balance, and then placed in a sample bottle. Later the temperature will be increased to approximately 90° C., so using a sample bottle which can withstand pressure is preferable. 10 mL of a reagent solution in which the concentration thereof had already been adjusted using purified water and TAE buffer solution (trisacetate ethylenediamine tetraacetic acid disodium salt solution) or the like, was measured in a pipette and added to the sample bottle. In order to detect LDH, the reagent solution was mixed with a 10 mM HEPES buffer solution which had been adjusted to pH 7 until the pyruvic acid concentration was 5 µM and the NADH concentration was 0.1 mM.

A magnetic stirrer was then added and the bottle sealed. The powder and the pure water were blended by mixing for approximately 30 seconds. Water was heated in a heating bath and the temperature was set to 90° C. The sample bottle was placed in the heating bath and stirred for 60 minutes or more using the stirrer until the solution was uniform. The reagent solution was added while mixing for between 1 and 12 hours at 65° C. in order to obtain transparency. Gas bubbles which occur during stirring can form in the gel, so the sample bottle was ultrasonically treated for several seconds to remove gas bubbles. Before cooling, 1.25 µL of the gel was placed in a 5 mm wide, 5 mm high, 0.05 mm thick reaction cell. The gel was allowed to set for two hours or more until a stable mesh structure was formed.

Detection Method

After heating the reagent in the structure 22 at 37° C. for three minutes, the collected whole blood was injected into a reaction cell 16 containing the structure 22. The whole blood collected in the injection port 12 was injected into the reaction cell without centrifugal separation by drawing the whole blood in the injection tube 14 from the discharge port 20 to the outside by a pump.

After the whole blood was injected, the LDH contained in the whole blood was diffused into the structure 22 formed from agarose while heating for 10 minutes at 37° C. While the LDH diffused into the structure 22, the reagent contained in the structure 22 and the LDH reacted as shown in the reaction formula (4).

(Reaction Formula 4)

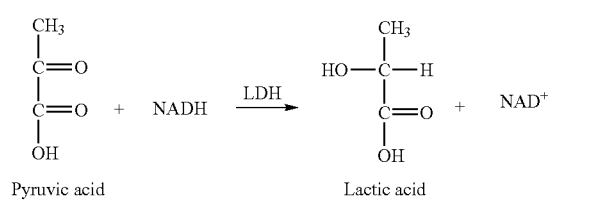

Pyruvic acid            Lactic acid (4)

The concentration and the reaction quantity of the NADH which was consumed by the reaction between the LDH and the reagent was measured for a predetermined period of time after the start time of contact between the LDH and the structure 22. The concentration was measured as shown below. A light source was inserted into the photoemission hole 18a established in the quantitative measurement chip 10 and light with a wavelength of 340 nm which is selectively absorbed by NADH was irradiated along the interface of a 1 mm×3 mm region of the structure 22. Furthermore, the light was received by an photoreceptor which had been inserted into the photoreception hole 18b, and thus the concentration of NADH was measured.

NADH is consumed by the reaction with LDH, so a correlation exists between the concentration of LDH and the concentration of the reaction product NADH. Furthermore, as the concentration of the LDH increases on the surface of the structure 22, or in other words as the concentration of LDH which has been injected into the reaction cell 16 increases, the diffusion speed of the LDH into the structure 22 will increase. Thus, the concentration of LDH on the surface of the agarose, or in other words the concentration of LDH in the whole blood, is quantitatively measured using the concentration of NADH detected based on a predetermined calibration curve. The calibration curve may be calculated by the same quantitative measurement methods using a reagent with a predetermined concentration of LDH and a structure 22 which has been prepared by the same method as above.

Test Results

Figure 9:
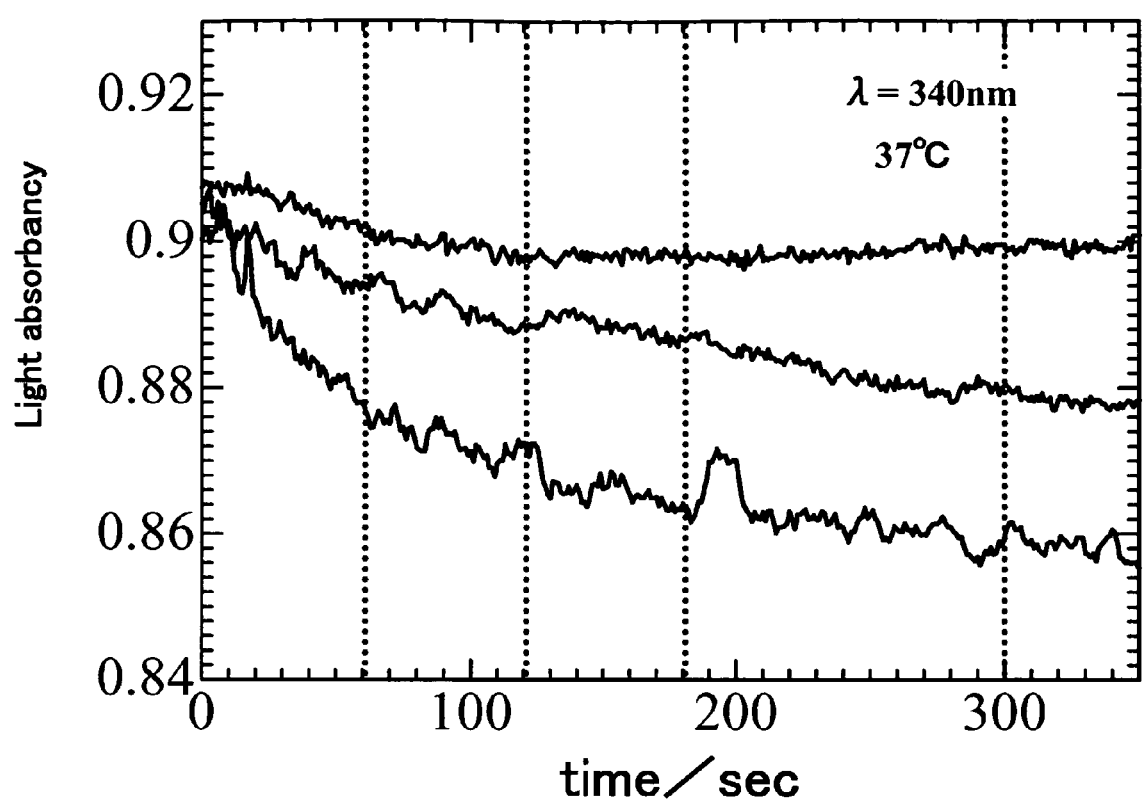
FIG. 9 shows the relationship between the time obtained from the test results and the light absorbency.

FIG. 9 shows the measured NADH light absorbency results for the case where three different concentrations of LDH were diffused into a structure 22 formed from agarose using the aforementioned method. The light absorbency of the NADH decreased over time. From the test results of FIG. 9, the change in NADH was accurately measured even by a one or two-minute test, and the concentration of LDH could be quantitatively measured from the light absorbency after a predetermined period of time had lapsed.

Furthermore, with this embodiment, the collected whole blood was introduced into the reaction cell 16 without centrifugal separation. With this embodiment, the enzyme LDH was made to react in a gelatinous substance which had a mesh of several tens of nanometers to several hundreds of nanometers. Thus, LDH which is smaller than the mesh would penetrate into the gelatinous substrate, without the red blood cells with a diameter of 7 μm and the white blood cells with a diameter of 15 μm penetrating into the gelatinous substance. In other words, the gelatinous substance functions as a blood cell filter so centrifugal separation is not necessary. In this manner, the gelatinous substance not only provides a location for reacting with the enzyme and for detecting light, but also acts as a blood cell component separator. Furthermore, the gelatinous substance also acts as a carrier for the reagent which is to react with the enzyme.

EXAMPLE 2

A test was performed concerning the diffusion distance for the case where the target substance was made to contact with the structure 22 shown above, and the required length T of the structure 22 was determined. The length T is defined as the length of the structure 22 in the direction which intersects with the contact interface A between the structure 22 and the target substance.

Figure 10:
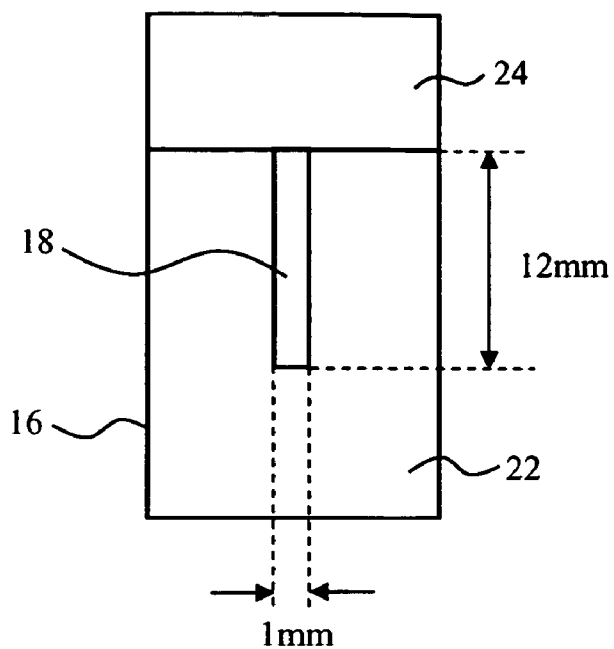
FIG. 10 shows a reaction cell for measuring the diffusion distance.

FIG. 10 shows a reaction cell for measuring the diffusion distance. The reaction cell 16 has a 1 mm×12 mm photoemission hole 18a and an photoreception hole 18b. A structure 22 and a contact unit 24 are established in the reaction cell 16. 1% Agarose was used for the structure 22. The dye (acid red) is injected into the contact unit 24 in the reaction cell 16, the reaction cell 16 is brought into contact with the structure 22 which consists of agarose.

Figure 11:
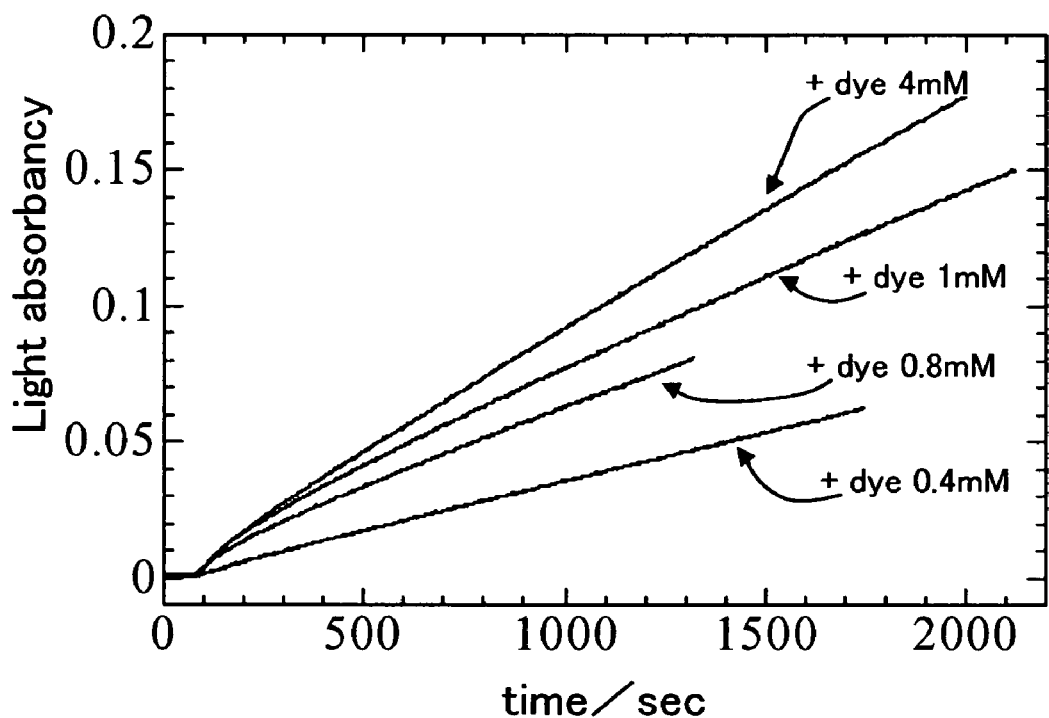
FIG. 11 shows the relationship between the measurement time and the light absorbency for the concentrations of acid red.

FIG. 11 shows the relationship between the quantitative measurement time and the light absorbency for 0.4 mM, 0.8 mM, 1.0 mM, and 4.0 mM concentrations of acid red. From FIG. 11, it can be seen that there was a difference in the level of absorbency for each concentration within approximately five minutes after the start of measurement. Thus, the concentration of the target substance acid red can be quantitatively measured by the absorbency after five minutes has lapsed from the start of the measurement.

Figure 12:
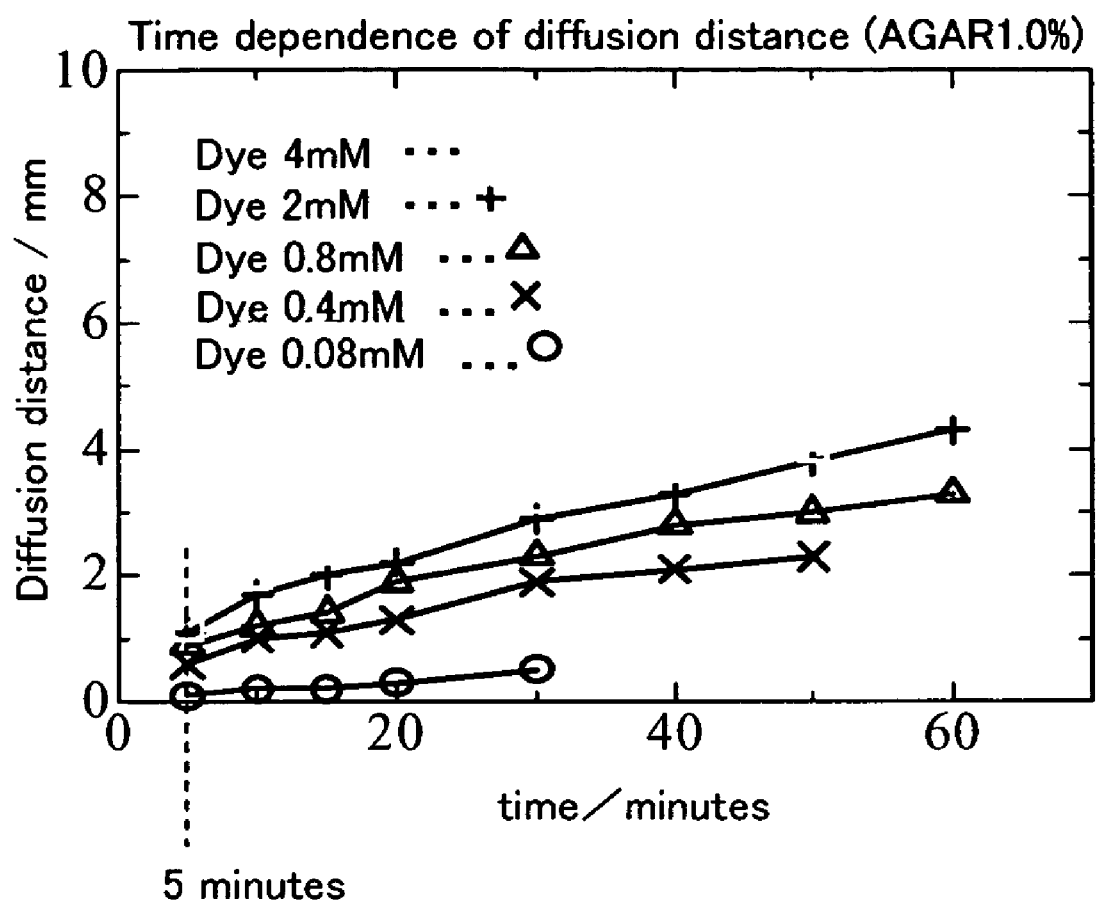
FIG. 12 shows the relationship between the diffusion distance of acid red in the structure and the quantitative measurement time.
Figure 13:
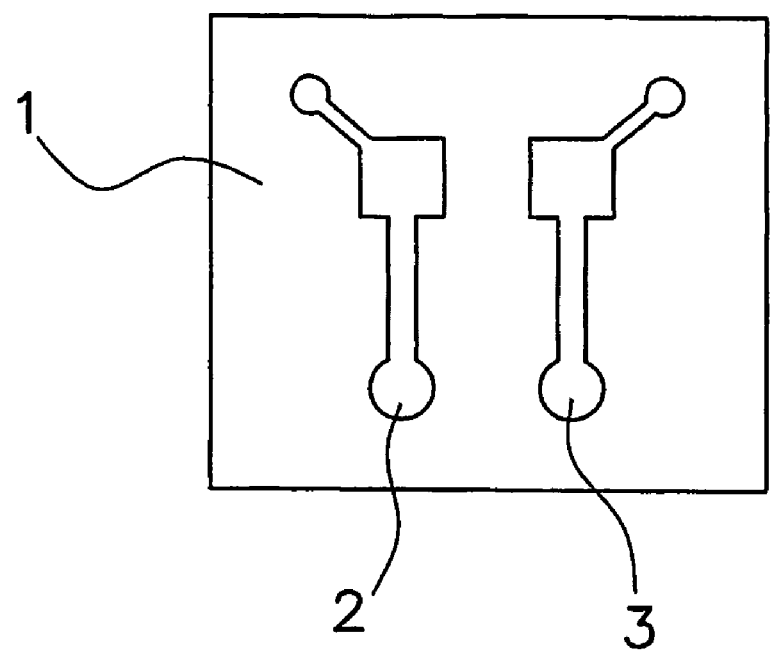
FIG. 13 shows a biochemical measurement chip disclosed in a publication titled "2002 International Conference on Solid State Devices and Substances".

FIG. 12 shows the relationship between the diffusion distance of acid red in the structure 22 and the quantitative measurement time for 0.08 mM, 0.4 mM, 0.8 mM, 2.0 mM, and 4.0 mM concentrations of acid red. The following results were obtained from FIG. 12.

- The diffusion distance for all concentrations after five minutes had lapsed from the start of measurement was less than approximately 1.5 mm.
- The diffusion distance for 0.08 mM acid red after five minutes had lapsed from the start of measurement was approximately 0.1 mm.
- The diffusion distance for 4.0 mM acid red after five minutes had lapsed from the start of measurement was approximately 1.0 mm.
- The diffusion distance for all concentrations after 60 minutes had lapsed from the start of measurement was less than approximately 5.0 mm.

Considering that the length T of the structure 22 must be larger than the diffusion distance of the target substance at the time of measurement, the length T of the structure 22 was decided as shown below. The diffusion distance for all concentrations after 5 minutes had lapsed was less than approximately 1.5 mm, so for the case where 1% agarose was used as the gelatinous material of the structure 22 and the measurement time was approximately 5 minutes, quantitative measurement of the target substance acid red could be performed if the length T of the structure 22 was approximately T=2.0 mm, because this length T is sufficiently thick enough to measure the diffusion distance of acid red. Furthermore, the diffusion distance for all concentrations after 60 minutes had lapsed was less than approximately 5.0 mm, so a measurement could be performed if the length T of the structure 22 was a maximum of approximately T=5.0 mm.

Furthermore, the diffusion distance after five minutes from the start of measurement for a relatively high acid red concentration of 4.0 mM was approximately 1.0 mm, so quantitative measurement can be performed on high concentrations of the target substance if the length T of the structure 22 is at least approximately T=1.0 mm. Furthermore, the diffusion distance after 5 minutes from the start of measurement for a relatively low acid red concentration of 0.08 mM was approximately 0.1 mm, so quantitative measurement can be performed on low concentrations of the target substance if the length T of the structure 22 is at least approximately T=0.1 mm.

From the foregoing, the results showed that the length T of the structure 22 under the above test conditions is preferably between 0.1 mm and 5.0 mm, and more preferably between 1.0 mm and 2.0 mm.

INDUSTRIAL APPLICABILITY

Using the present invention, a quantitative measurement method and a quantitative measurement chip which can perform quantitative measurement of a target substance in a short period of time can be provided.

In addition, using the present invention, a quantitative measurement method and quantitative measurement chip which can simplify quantitative measurement of the target substance can be provided.

In addition, using the present invention, a quantitative measurement method and a quantitative measurement chip which can accurately measure the target substance can be provided.

Furthermore, using the present invention, a quantitative measurement method and a quantitative measurement chip which can prevent leaking of the test reagent can be provided.

What is claimed is:

1. A quantitative measurement method, comprising the steps of:
    (a) bringing a test specimen containing a target substance into contact with a material having a three dimensional mesh structure which contains a reagent that reacts with the target substance;
    (b) detecting, at a contact interface between the test specimen and the reagent, a substance whose quantity increases or decreases within the mesh structure by means of the reaction between the target substance and the reagent; and
    (c) performing quantitative measurement of the target substance in response to the results of step (b);
    wherein the mesh structure allows at least the target substance to pass therethrough.

2. The quantitative measurement method according to claim 1, wherein the mesh structure is sized to prevent components of the test specimen which is are larger than the target substance from passing therethrough.

3. The quantitative measurement method according to claim 1, wherein the test specimen is whole blood, and the target substance is the blood plasma component thereof.

4. The quantitative measurement method according to claim 1, wherein in step (b), the concentration of the quantitatively increasing or decreasing substance is measured at a predetermined distance from the contact interface after a predetermined period of time has elapsed from the time at which the test specimen came into contact with the mesh structure in step (a).

5. The quantitative measurement method according to claim 1, wherein in step (b), the time until a predetermined concentration of the quantitatively increasing or decreasing substance is detected at a predetermined distance from the contact interface will be measured based upon the time at which the test specimen first came into contact with the mesh structure in step (a).

6. The quantitative measurement method according to claim 1, wherein in step (b), the distance from the contact interface to the position where the quantitatively increasing or decreasing substance is detected will be measured, after a predetermined period of time has elapsed from the time at which the test specimen first came into contact with the mesh structure in step (a).

7. The quantitative measurement method according to claim 1, wherein in step (b), the concentration distribution of the quantitatively increasing or decreasing substance is detected at a distance from the contact interface by scanning the mesh structure after step (a).

8. The quantitative measurement method according to claim 1, wherein in step (b), the quantitatively increasing or decreasing substance is detected by measuring the light absorbency thereof.

9. The quantitative measurement method according to claim 1, further comprising the step of applying a voltage to the target substance having an electrical charge in order to promote the diffusion of the target substance into the mesh structure.

10. A quantitative measurement chip comprising:
    a reaction cell that is formed with a material having a three dimensional mesh structure which contains a reagent that reacts with a target substance contained in a test specimen;
    a photoemitter and a photoreceptor for measuring, at a contact interface between the test specimen and the reagent, the light absorbance of a substance whose quantity increases or decreases within the reaction cell by means of the reaction between the target substance and the reagent; and
    an injection tube for injecting the test specimen containing the target substance into the reaction cell;
    wherein the mesh structure allows at least the target substance to pass therethrough.

11. The quantitative measurement chip according to claim 10, wherein the mesh structure is sized to prevent components of the test specimen which are larger than the target substance from passing therethrough.

12. The quantitative measurement chip according to claim 10, wherein the planar direction of the photoemission surface of the photoemitter and the planar direction of the photoreception surface of the photoreceptor intersect with the planar direction of the contact interface.

13. The quantitative measurement chip according to claim 10, wherein the photoemitter and the photoreceptor are respectively formed from a photoemission hole for irradiating light into the mesh structure and a photoreception hole which receives light from the mesh structure.

* * * * *